United States Patent
Merkel et al.

(10) Patent No.: US 8,034,251 B2
(45) Date of Patent: Oct. 11, 2011

(54) AZEOTROPIC COMPOSITIONS OF 2-CHLORO-3,3,3-TRIFLUOROPROPENE (HCFC-1233XF), 2-CHLORO-1,1,1,2-TETRAFLUOROPROPANE (HCFC-244BB), AND HYDROGEN FLUORIDE (HF)

(75) Inventors: Daniel C. Merkel, West Seneca, NY (US); Konstantin A. Pokrovski, Orchard Park, NY (US); Hsuehsung Tung, Getzville, NY (US); Hang T. Pham, Amherst, NY (US); Rajiv R. Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 51 days.

(21) Appl. No.: 12/406,653

(22) Filed: Mar. 18, 2009

(65) Prior Publication Data

US 2011/0210289 A9    Sep. 1, 2011

Related U.S. Application Data

(63) Continuation-in-part of application No. 11/619,592, filed on Jan. 3, 2007.

(60) Provisional application No. 61/043,451, filed on Apr. 9, 2008.

(51) Int. Cl.
  *C09K 5/04* (2006.01)
  *C11D 7/50* (2006.01)
  *C07C 17/383* (2006.01)

(52) U.S. Cl. .......... 252/67; 510/177; 510/410; 510/408; 570/155; 570/177

(58) Field of Classification Search .................. 252/67; 510/177, 410, 408; 570/155, 177
See application file for complete search history.

(56) References Cited

U.S. PATENT DOCUMENTS

| | | | |
|---|---|---|---|
| 2002/0142927 A1 | 10/2002 | Pham et al. | 510/177 |
| 2007/0007488 A1 | 1/2007 | Singh et al. | 252/68 |
| 2007/0197842 A1 | 8/2007 | Mukhopadhyay et al. | 570/155 |

FOREIGN PATENT DOCUMENTS

| | | |
|---|---|---|
| WO | WO2007/079431 | 7/2007 |
| WO | WO2008/054781 | 5/2008 |
| WO | WO2009/003084 | 12/2008 |
| WO | WO2009/009421 | 1/2009 |

OTHER PUBLICATIONS

CAS reg. No. 1190755-02-2, Oct. 30, 2009.*
CAS reg. No. 7664-39-3, Nov. 16, 1984.*
CAS reg. No. 2730-62-3, Nov. 16, 1984.*
CAS reg. No. 421-73-8, Nov. 16, 1984.*
U.S. Appl. No. 61/148,246, filed Jan. 29, 2009.
U.S. Appl. No. 61/113,477, filed Nov. 11, 2008.
U.S. Appl. No. 61/053,518, filed May 15, 2008.
U.S. Appl. No. 61/040,759, filed May 31, 2008.

* cited by examiner

*Primary Examiner* — Douglas McGinty
(74) *Attorney, Agent, or Firm* — Bruce Bradford

(57) ABSTRACT

Provided are ternary azeotropic and azeotrope-like compositions of 2-chloro-3,3,3-trifluoropropene (HCFO-1233xf), 2-chloro-1,1,1,2-tetrafluoropropane (HCFC-244bb), and hydrogen fluoride (HF). Such azeotropic and azeotrope-like compositions are useful as intermediates in the production of 2,3,3,3-tetrafluoropropene (HFO-1234yf).

25 Claims, No Drawings

US 8,034,251 B2

AZEOTROPIC COMPOSITIONS OF 2-CHLORO-3,3,3-TRIFLUOROPROPENE (HCFC-1233XF), 2-CHLORO-1,1,1,2-TETRAFLUOROPROPANE (HCFC-244BB), AND HYDROGEN FLUORIDE (HF)

CROSS REFERENCE TO RELATED APPLICATION

This application claims the benefit of U.S. Provisional patent application Ser. No. 61/043,451 filed Apr. 9, 2008, which is incorporated herein by reference. The present application is also a continuation-in-part of U.S. patent application Ser. No. 11/619,592, filed Jan. 3, 2007.

BACKGROUND OF THE INVENTION

1. Field of the Invention

The present invention pertains to ternary azeotropic and azeotrope-like compositions of 2-chloro-3,3,3-trifluoropropene (HCFO-1233xf), 2-chloro-1,1,1,2-tetrafluoropropane (HCFC-244bb), and hydrogen fluoride (HF). More particularly the invention pertains to such ternary azeotropic and azeotrope-like compositions which are useful as intermediates in the production of 2,3,3,3-tetrafluoropropene (HFO-1234yf).

2. Description of the Related Art

Traditionally, chlorofluorocarbons (CFCs) like trichlorofluoromethane and dichlorodifluoromethane have been used as refrigerants, blowing agents and diluents for gaseous sterilization. In recent years there has been universal concern that completely halogenated chlorofluorocarbons might be detrimental to the Earth's ozone layer. Therefore, stratospherically safer alternatives to these materials are desirable. Consequently, there is a worldwide effort to use fluorine-substituted hydrocarbons which contain fewer or no chlorine substituents. In this regard, 2-chloro-3,3,3-trifluoropropene (HCFO-1233xf) and 2-chloro-1,1,1,2-tetrafluoropropane (HCFC-244bb), having low ozone depletion potential, are being considered as a replacement for chlorofluorocarbons such as dichlorodifluoromethane in refrigeration systems and trichlorofluoromethane as a blowing agent. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are not non-ozone depleting, but also they are non-flammable, and non-toxic as compared to the chlorine containing compounds.

HCFO-1233xf and HCFC-244bb are intermediates in the production of 2,3,3,3-tetrafluoropropene (HFO-1234yf) which is well known in the art as described in U.S. Applications 20070007488 and 20070197842, the specifications of which are incorporated herein by reference. HFO-1234yf has been disclosed to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid.

It has now been found that an important intermediate in the production of substantially pure HFO-1234yf, is a ternary azeotropic or azeotrope-like composition of 2-chloro-3,3,3-trifluoropropene (HCFO-1233xf), 2-chloro-1,1,1,2-tetrafluoropropane (HCFC-244bb), and hydrogen fluoride. This intermediate, once formed, may thereafter be separated into its component parts by known extraction techniques. The ternary azeotropic and azeotrope-like compositions find use not only as intermediates in the production of HFO-1234yf, but they are additionally useful as nonaqueous etchant mixtures for etching semiconductors in the electronics industry, as well as compositions for removing surface oxidation from metals. In addition, the formation of a ternary azeotropic or azeotrope-like composition of 2-chloro-3,3,3-trifluoropropene (HCFO-1233xf), 2-chloro-1,1,1,2-tetrafluoropropane (HCFC-244bb), and hydrogen fluoride is useful in separating a mixture of HCFO-1233xf and HCFC-244bb from another component such as a halocarbon, for example, 1,1,1,2,3-pentachloropropane; 1,1,2,3-tetrachloropropene; 2,3,3,3-tetrafluoropropene; 2,3-dichloro-3,3-difluoropropene; 1,1,1,2,2-pentafluoropropane; or 1,2-dichloro-3,3,3-trifluoropropene. When it is desired to separate a mixture of HCFO-1233xf and HCFC-244bb from another component, HF is added to form a ternary azeotropic mixture of HCFO-1233xf, HCFC-244bb and hydrogen fluoride, and then the another component is removed from the ternary azeotropic mixture, such as by distillation or other known means. This ternary azeotrope or azeotrope-like composition is then available for separation into its component parts.

SUMMARY OF THE INVENTION

The invention provides a ternary azeotropic or azeotrope-like composition comprising hydrogen fluoride, 2-chloro-3,3,3-trifluoropropene, and 2-chloro-1,1,1,2-tetrafluoropropane.

The invention also provides a ternary azeotropic or azeotrope-like composition consisting essentially of hydrogen fluoride, 2-chloro-3,3,3-trifluoropropene, and 2-chloro-1,1,1,2-tetrafluoropropane.

The invention also provides a combination comprising a ternary azeotropic or azeotrope-like composition consisting essentially of hydrogen fluoride, 2-chloro-3,3,3-trifluoropropene, and 2-chloro-1,1,1,2-tetrafluoropropane.

The invention further provides an azeotropic or azeotrope-like composition which consists essentially of from about 1 to about 50 weight percent hydrogen fluoride, from about 50 to about 99 weight percent of an organic portion consisting essentially of a mixture of 2-chloro-3,3,3-trifluoropropene and 2-chloro-1,1,1,2-tetrafluoropropane, wherein the 2-chloro-3,3,3-trifluoropropene in the organic portion of the mixture is present in the amount from about 50 to about 90 weight percent of the organic portion, and the 2-chloro-1,1,1,2-tetrafluoropropane in the organic portion of the mixture is present in the amount from about 10 to about 50 weight percent of the organic portion, and the azeotropic composition has a boiling point of from about 0° C. to about 61° C. at a pressure of from about 15 psia to about 108 psia.

The invention further provides a method of forming a ternary azeotropic or azeotrope-like composition which comprises forming a blend comprising hydrogen fluoride, 2-chloro-3,3,3-trifluoropropene, and 2-chloro-1,1,1,2-tetrafluoropropane.

The invention further provides a method of forming a ternary azeotropic or azeotrope-like composition which comprises forming a blend consisting essentially of hydrogen fluoride, 2-chloro-3,3,3-trifluoropropene, and 2-chloro-1,1,1,2-tetrafluoropropane.

The invention further provides a method of forming a ternary azeotropic or azeotrope-like composition which comprises forming a blend consisting essentially of from about 1 to about 50 weight percent hydrogen fluoride, and from about 50 to about 99 weight percent of an organic portion consisting essentially of a mixture of 2-chloro-3,3,3-trifluoropropene and 2-chloro-1,1,1,2-tetrafluoropropane, wherein the 2-chloro-3,3,3-trifluoropropene in the organic portion of the mixture is present in the amount from about 50 to about 90 weight percent of the organic portion, and the 2-chloro-1,1,1,2-tetrafluoropropane in the organic portion of the mixture is present in the amount from about 10 to about 50 weight percent of the organic portion, and the azeotropic composition has a boiling point of from about 0° C. to about 61° C. at a pressure of from about 15 psia to about 108 psia.

The invention also provides a method for removing 2-chloro-3,3,3-trifluoropropene and 2-chloro-1,1,1,2-tetrafluoropropane from a mixture containing 2-chloro-3,3,3-trifluoropropene, 2-chloro-1,1,1,2-tetrafluoropropane, and at least one other component, which comprises adding hydrogen fluoride to the mixture in an amount sufficient to form a ternary azeotropic or azeotrope-like composition of the hydrogen fluoride, 2-chloro-3,3,3-trifluoropropene, and 2-chloro-1,1,1,2-tetrafluoropropane, and thereafter separating the ternary azeotropic composition from the other component.

DETAILED DESCRIPTION OF THE INVENTION

In a method of preparing a HCFC-244bb precursor, reagents are fluorinated with hydrogen fluoride. This may be done, for example, by the liquid phase or gas phase catalytic fluorination of $CF_3CCl=CH_2$ (HCFO-1233xf) with HF to yield HCFC-244bb. Such methods are disclosed in U.S. Applications 20070007488 and 20070197842. The reaction products of such precursors include HCFC-244bb, unreacted HCFO-1233xf and HF, and other by-products. Upon removal of the by-products, a ternary azeotrope or azeotrope-like composition of HCFO-1233xf, HCFC-244bb and HF is formed. This ternary azeotrope or azeotrope-like composition is then available for separation into its component parts. The azeotropic or azeotrope-like compositions of the HCFO-1233xf, HCFC-244bb and HF are also useful as recycle to the fluorination reactor. Thus, for example, in a process for producing HCFC-244bb, one can recover a portion of the HCFO-1233xf and HCFC-244bb as an azeotropic or azeotrope-like composition of HCFO-1233xf, HCFC-244bb and HF and then recycle the composition to the reactor.

In a method of preparing a HCFO-1233xf precursor, reagents are fluorinated with hydrogen fluoride. This may be done, for example, by the gas phase catalytic fluorination of $CCl_2=CClCH_2Cl$ with HF to yield HCFO-1233xf. Such methods are disclosed in U.S. Application 20070197842, the specification of which is incorporated herein by reference. The reaction products of such precursors include HCFO-1233xf, over-fluorinated species such as HCFC-244bb, unreacted HF and other by-products. Upon removal of the by-products, a ternary azeotrope or azeotrope-like composition of HCFO-1233xf, HCFC-244bb and HF is formed. This ternary azeotrope or azeotrope-like composition is then available for separation into its component parts. The azeotropic or azeotrope-like compositions of the HCFO-1233xf, HCFC-244bb and HF are also useful as feed to the HCFO-1233xf fluorination reactor as disclosed in U.S. Applications 20070007488 and 20070197842. Thus, for example, in a process for producing HCFO-1233xf, one can recover a portion of the HCFO-1233xf and HCFC-244bb as an azeotropic or azeotrope-like composition of HCFO-1233xf, HCFC-244bb and HF and then feed it forward to the HCFO-1233xf fluorination reactor.

A mixture of HCFC-244bb and HCFO-1233xf forms azeotropic and azeotrope-like mixtures with HF. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions, which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises amounts of HCFO-1233xf and HCFC-244bb and hydrogen fluoride effective to form an azeotropic or azeotrope-like composition. By effective amount is meant an amount of each component which, when combined with the other component, results in the formation of an azeotrope or azeotrope-like mixture. The inventive compositions preferably are ternary azeotropes which consist essentially of combinations of only HCFO-1233xf and HCFC-244bb and hydrogen fluoride.

In a preferred embodiment, the inventive composition contains from about 1 to about 50 weight percent HF, preferably from about 5 weight percent to about 40 weight percent and more preferably from about 10 weight percent to about 35 weight percent based on the weight of the ternary azeotropic or azeotrope-like composition.

The inventive azeotropic or azeotrope-like composition then contains from about 50 to about 99 weight percent of an organic portion consisting essentially of a combination of HCFC-244bb and HCFO-1233xf, preferably from about 60 weight percent to about 95 weight percent and more preferably from about 65 weight percent to about 90 weight percent based on the weight of the azeotropic or azeotrope-like composition.

In a preferred embodiment, the organic portion of the azeotropic or azeotrope-like composition, that is a mixture of HCFC-244bb/HCFO-1233xf mixture contains from about 50 to about 90 weight percent HCFO-1233xf, preferably from about 51.5 weight percent to about 86.5 weight percent and more preferably from about 53 weight percent to about 83 weight percent based on the weight of the organic portion of the azeotropic or azeotrope-like composition.

In a preferred embodiment, the organic portion of the azeotropic or azeotrope-like composition, that is a mixture of HCFC-244bb/HCFO-1233xf mixture contains from about 10 to about 50 weight percent HCFC-244bb, preferably from about 13.5 weight percent to about 48.5 weight percent and more preferably from about 17 weight percent to about 47 weight percent based on the weight of the organic portion of the azeotropic or azeotrope-like composition.

The composition of the present invention preferably has a boiling point of about from 0° C. to about 61° C. at a pressure of about 15 psia to about 108 psia. In one embodiment it has a boiling point of about 23° C. at a pressure of about 37 psia. In another embodiment it has a boiling point of about 0° C. at a pressure of about 15 psia. In another embodiment it has a boiling point of about 61° C. at a pressure of about 108 psia.

In another embodiment of the invention, 2-chloro-3,3,3-trifluoropropene (HCFO-1233xf) and 2-chloro-1,1,1,2-tetrafluoropropane (HCFC-244bb) may be removed from a mixture containing 2-chloro-3,3,3-trifluoropropene (HCFO-1233xf), 2-chloro-1,1,1,2-tetrafluoropropane (HCFC-244bb), and another component which may, for example, result from manufacturing steps in the preparation of 2-chloro-1,1,1,2-tetrafluoropropane (HCFC-244bb) and/or 2-chloro-3,3,3-trifluoropropene (HCFO-1233xf). This is done by adding hydrogen fluoride to the mixture of the 2-chloro-1,1,1,2-tetrafluoropropane (HCFC-244bb), 2-chloro-3,3,3-trifluoropropene (HCFO-1233xf) and another component. Hydrogen fluoride is added to the mixture in an amount sufficient to form an azeotropic composition of the 2-chloro-1,1,1,2-tetrafluoropropane (HCFC-244bb), 2-chloro-3,3,3-trifluoropropene (HCFO-1233xf) and the hydrogen fluoride, and thereafter the azeotropic composition is separated from the another component, for example by distillation or other art recognized separating means. In one embodiment, the another component itself does not form an azeotropic mixture with 2-chloro-1,1,1,2-tetrafluoropropane (HCFC-244bb), 2-chloro-3,3,3-trifluoropropene (HCFO-1233xf), or hydrogen fluoride individually, or a mixture of 2-chloro-1,1,1,2-tetrafluoropropane (HCFC-244bb), 2-chloro-3,3,3-trifluoropropene (HCFO-1233xf), and hydrogen fluoride. In another embodiment, the another component does form an azeotropic mixture with 2-chloro-1,1,1,2-tetrafluoropropane (HCFC-244bb), 2-chloro-3,3,3-trifluoropropene (HCFO-1233xf), or hydrogen fluoride individually or a mixture of 2-chloro-1,1,1,2-tetrafluoropropane (HCFC-244bb), 2-chloro-3,3,3-trifluoropropene (HCFO-1233xf), and hydrogen fluoride. Typical impurities include other halocarbons which may be miscible with HCFC-244bb or HCFO-1233xf such as 1,1,1,2,3-pentachloropropane; 1,1,2,3-tetrachloropropene; 2,3,3,3-tetrafluoropropene; 2,3-dichloro-3,3-difluoropropene (HCFO-1232xf); 1,1,1,2,2-pentafluoropropane; or 1,2-dichloro-3,3,3-trifluoropropene.

The following non-limiting examples serve to illustrate the invention.

Example 1

37.4 pounds of the material containing 3 weight percent HF balanced with mixture of organics consisting of 44.4 weight percent HCFC-244bb and 55.6 weight percent HCFO-1233xf was charged into the distillation column. The mixture was homogeneous. The distillation column consisted of a 10 gallon reboiler, 2 inch ID by 8 feet propack column, and a shell and tube condenser. The column had about 30 theoretical plates. The distillation column was equipped with temperature, pressure, and differential pressure transmitters. The distillation was run at pressure of about 23-25 psig. The distillate was sampled, titrated for HF concentration determination, and analyzed by GC at regular intervals. Analysis showed a ternary azeotrope of HF/HCFC-244bb/HCFO-1233xf. The HF concentration of the azeotrope was analyzed to be about 25-33 wt % HF using titration with 0.1 N KOH. The organic concentration based on GC area % was about 17-21 GC area % HCFC-244bb and about 79-83 GC area % HCFO-1233xf. At a pressure of 23-25 psig the column overhead temperature was about 23° C. for this composition.

Example 2

The following example used a Monel distillation column consisting of a 2 liter reboiler, 1 inch ID×4 feet long helicoil packed column, and tube and shell condenser. The column was equipped with temperature, pressure, and differential pressure transmitters. 1000 grams of material containing about 3.2 wt % HF balanced with mixture of organics consisting of about 51 weight percent HCFC-244bb and 49 weight percent HCFO-1233xf were charged into the distillation system. The mixture was homogeneous. The distillation was performed at a pressure 7-29 psig. Analysis of distillate samples showed consistent results at a pressure above 18 psig. The organic composition by GC was determined to be about 21-23 GC Area % HCFC-244bb and about 79-77 GC Area % HCFO-1233xf and the concentration of HF in the distillate was found to be about 25-29 weight % HF using titration with 0.1 N NaOH. The decrease in the amount of HF in the sample occurred sharply indicating a ternary azeotrope of HCFC-244bb/HCFO-1233xf/HF.

Example 3

Ternary compositions containing a mixture of 2-chloro-3,3,3-trifluoropropene (HCFO-1233xf) and 2-chloro-1,1,1,2-tetrafluoropropane (HCFC-244bb) (50/50%) and HF were blended to form a ternary heterogeneous azeotrope mixtures at different compositions. The vapor pressures of the mixtures were measured at about 0, 25 and 61° C. and the following results were noticed. Table 1 shows the vapor pressure measurements of HCFO-1233xf, HCFC-244bb, and HF as a function of composition with varying weight percent HF at constant temperatures of about 0° C., 25° C., and 61° C. The data also showed that in this range of hydrogen fluoride concentration the mixture of HCFO-1233xf/HCFC-244bb/HF is heterogeneous.

TABLE 1

P-T-X of [HCFO-1233xf/HCFC-244bb (50/50%)]/HF

| Wt. % HF | Pressure (Psia) | | |
|---|---|---|---|
| | T = 0° C. | T = 25° C. | T = 61° C. |
| 0 | 9.4 | 23.8 | 65.0 |
| 7.29 | 15.2 | 38.4 | 104.0 |
| 14.59 | 15.2 | 38.5 | 107.7 |
| 22.13 | 15.1 | 38.4 | 107.2 |
| 31.60 | 15.1 | 38.3 | 107.2 |
| 37.32 | 15.1 | 38.5 | 107.2 |
| 100.0 | 6.87 | 17.8 | 52.4 |

The data also show that the mixture is azeotropic or azeotrope-like since the vapor pressure of the ternary mixtures of HCFO-1233xf/HCFC-244bb (50/50%) and HF is higher, at all indicated blend proportions, than vapor pressures of HCFO-1233xf/HCFC-244bb (50/50%) and HF alone, i.e. as indicated in the first and last rows of Table 1 when HF is 0.0 wt. % and HCFO-1233xf/HCFC-244bb is at 100.0 wt. % as well as when HCFO-1233xf/HCFC-244bb (50/50%) is at 0.0 wt. % and HF is at 100.0 wt. %.

Example 4

The azeotropic or azeotrope-like composition of the ternary (HCFO-1233xf/HCFC-244bb)(50/50%)/HF mixture was also verified by Vapor-Liquid-Liquid equilibrium (VLLE) experiment. 13 g of HCFO-1233xf/HCFC-244bb (50/50%) were mixed with 7.8 g of HF to form a heterogeneous mixture (visual observation) at 23° C. The vapor composition was sampled. The result shows that the vapor composition is about 18±2 wt. % HF at 23° C.

Example 5

The azeotropic or azeotrope-like composition of the ternary (HCFO-1233xf/HCFC-244bb)(50/50%)/HF mixture was also verified by Vapor-Liquid-Liquid equilibrium (VLLE) experiment. 38.9 g of HCFO-1233xf/HCFC-244bb (5050%) were mixed with 37.3 g of HF to form a heterogeneous mixture (visual observation) at 23° C. The vapor composition and the organic rich layer were sampled. The result shows that the vapor composition is about 14±2 wt. % HF at 23° C., consistent with the results obtained in the other two-phase region experiment described in Example 4.

Example 6

The azeotropic or azeotrope-like composition of the ternary (HCFO-1233xf/HCFC-244bb)(50/50%)/HF mixture was also verified by Vapor-Liquid-Liquid equilibrium (VLLE) experiment. 9 g of HCFO-1233xf/HCFC-244bb (50/50%) were mixed with 15 g of HF to form a homogeneous mixture (visual observation) at 23° C. The vapor composition was sampled. The result shows that the vapor composition is about 31±2 wt. % HF at 23° C. This observation is in agreement with examples 1 and 2 for the single phase (homogeneous) region.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above, and all equivalents thereto.

What is claimed is:

1. A ternary azeotropic or azeotrope-like composition consisting essentially of hydrogen fluoride, 2-chloro-3,3,3-trifluoropropene, and 2-chloro-1,1,1,2-tetrafluoropropane.

2. An azeotropic or azeotrope-like composition which consists essentially of from about 1 to about 50 weight percent hydrogen fluoride, from about 50 to about 99 weight percent of an organic portion consisting essentially of 2-chloro-3,3,3-trifluoropropene and 2-chloro-1,1,1,2-tetrafluoropropane, wherein the 2-chloro-3,3,3-trifluoropropene in the organic portion of the mixture is present in the amount from about 50 to about 90 weight percent of the organic portion, and the 2-chloro-1,1,1,2-tetrafluoropropane in the organic portion of the mixture is present in the amount from about 10 to about 50 weight percent of the organic portion, and the azeotropic composition has a boiling point of from about 0° C. to about 61° C. at a pressure of from about 15 psia to about 108 psia.

3. The composition of claim 2 which consists of hydrogen fluoride, 2-chloro-3,3,3-trifluoropropene, and 2-chloro-1,1,1,2-tetrafluoropropane.

4. The composition of claim 2 wherein the hydrogen fluoride is present in the amount from about 5 to about 40 weight percent.

5. The composition of claim 2 wherein the organic portion is present in the amount from about 60 to about 95 weight percent.

6. The composition of claim 2 wherein the 2-chloro-3,3,3-trifluoropropene in the organic portion is present in the amount from about 51.5 to about 86.5 weight percent of the organic portion.

7. The composition of claim 2 wherein the 2-chloro-1,1,1,2-tetrafluoropropane in the organic portion of the azeotrope is present in the amount from about 13.5 to about 48.5 weight percent of the organic portion.

8. The composition of claim 2 having a boiling point of about 23° C. at a pressure of about 37 psia; or a boiling point of about 0° C. at a pressure of about 15 psia; or a boiling point of about 61° C. at a pressure of about 108 psia.

9. A method of forming an azeotropic or azeotrope-like composition which comprises forming a blend consisting essentially of from about 1 to about 50 weight percent hydrogen fluoride, from about 50 to about 99 weight percent of an organic portion consisting essentially of 2-chloro-3,3,3-trifluoropropene and 2-chloro-1,1,1,2-tetrafluoropropane, wherein the 2-chloro-3,3,3-trifluoropropene in the organic portion of the mixture is present in the amount from about 50 to about 90 weight percent of the organic portion, and the 2-chloro-1,1,1,2-tetrafluoropropane in the organic portion of the mixture is present in the amount from about 10 to about 50 weight percent of the organic portion to thereby form an azeotropic or azeotrpic-like composition having a boiling point of from about 0° C. to about 61° C. at a pressure of from about 15 psia to about 108 psia.

10. The method of claim 9 wherein the azeotropic or azeotrope-like composition consists of hydrogen fluoride, 2-chloro-3,3,3-trifluoropropene, and 2-chloro-1,1,1,2-tetrafluoropropane.

11. The method of claim 9 wherein the hydrogen fluoride is present in the amount from about 5 to about 40 weight percent.

12. The method of claim 9 wherein the organic portion is present in the amount from about 60 to about 95 weight percent.

13. The method of claim 9 wherein the 2-chloro-3,3,3-trifluoropropene in the organic portion is present in the amount from about 51.5 to about 86.5 weight percent of the organic portion.

14. The method of claim 9 wherein the 2-chloro-1,1,1,2-tetrafluoropropane in the organic portion of the azeotrope is present in the amount from about 13.5 to about 48.5 weight percent of the organic portion.

15. The method of claim 9 wherein the azeotropic or azeotrope-like composition has a boiling point of about 23° C. at a pressure of about 37 psia; or a boiling point of about 0° C. at a pressure of about 15 psia; or a boiling point of about 61° C. at a pressure of about 108 psia.

16. The method of claim 9 further comprising the step of feeding the azeotropic or azeotropic-like composition of 2-chloro-3,3,3-trifluoropropene, 2-chloro-1,1,1,2-tetrafluoropropane and hydrogen fluoride to a fluorination reactor.

17. The method of claim 9 further comprising the step of separating 2-chloro-3,3,3-trifluoropropene and 2-chloro-1,1,1,2-tetrafluoropropane from an azeotropic or azeotropic-like composition of hydrogen fluoride, 2-chloro-3,3,3-trifluoropropene, and 2-chloro-1,1,1,2-tetrafluoropropane by pressure swing distillation.

18. A method for removing 2-chloro-3,3,3-trifluoropropene and 2-chloro-1,1,1,2-tetrafluoropropane from a mixture containing 2-chloro-3,3,3-trifluoropropene, 2-chloro-1,1,1,2-tetrafluoropropane and at least one other component, which comprises adding hydrogen fluoride to the mixture in an amount sufficient to form a ternary azeotropic or azeotrope-like composition of the hydrogen fluoride, 2-chloro-3,3,3-trifluoropropene and 2-chloro-1,1,1,2-tetrafluoropropane and thereafter separating the ternary azeotropic composition from the at least one other component.

19. The method of claim 18 wherein the at least one other component does not form an azeotropic mixture with 2-chloro-3,3,3-trifluoropropene, 2-chloro-1,1,1,2-tetrafluoropropane, hydrogen fluoride or a mixture of 2-chloro-3,3,3-trifluoropropene, 2-chloro-1,1,1,2-tetrafluoropropane, and hydrogen fluoride.

20. The method of claim 18 wherein the at least one other component does form an azeotropic mixture with 2-chloro-3,3,3-trifluoropropene, 2-chloro-1,1,1,2-tetrafluoropropane, hydrogen fluoride or a mixture of 2-chloro-3,3,3-trifluoropropene, 2-chloro-1,1,1,2-tetrafluoropropane, and hydrogen fluoride.

21. The method of claim 18 wherein the at least one other component comprises a halocarbon.

22. The method of claim 18 wherein the at least one other component comprises one or more of 1,1,1,2,3-pentachloropropane; 1,1,2,3-tetrachloropropene; 2,3,3,3-tetrafluoropropene; 2,3-dichloro-3,3-difluoropropene; 1,1,1,2,2-pentafluoropropane; and 1,2-dichloro-3,3,3-trifluoropropene.

23. The method of claim 18 wherein the separating is conducted by distillation.

24. The method of claim 18 wherein the azeotropic composition consists essentially of from about 1 to about 50 weight percent hydrogen fluoride, and from about 50 to about 99 weight percent of an organic portion consisting essentially of a mixture of 2-chloro-3,3,3-trifluoropropene and 2-chloro-1,1,1,2-tetrafluoropropane, wherein the 2-chloro-3,3,3-trifluoropropene in the organic portion of the mixture is present in the amount from about 50 to about 90 weight percent of the organic portion, and the 2-chloro-1,1,1,2-tetrafluoropropane in the organic portion of the mixture is present in the amount from about 10 to about 50 weight percent of the organic portion.

25. The method of claim 18 wherein the azeotropic composition consists essentially of from about 5 to about 40 weight percent hydrogen fluoride, and from about 60 to about 95 weight percent of the organic portion, and the 2-chloro-3,3,3-trifluoropropene in the organic portion of the mixture is present in an amount from about 51.5 to about 86.5 weight percent of the organic portion, and the 2-chloro-1,1,1,2-tetrafluoropropane in the organic portion of the mixture is present in the amount from about 13.5 to about 48.5 weight percent of the organic portion.

* * * * *